(12) United States Patent
Hla et al.

(10) Patent No.: US 9,592,268 B2
(45) Date of Patent: Mar. 14, 2017

(54) ENDOTHELIUM PROTECTIVE MATERIALS AND METHODS OF USE

(75) Inventors: Timothy Hla, Avon, CT (US); Hideru Obinata, New York, NY (US); Sylvain Galvani, New York, NY (US); Bjorn Dahlback, Malmo (SE); Lars Bo Nielsen, Copenhagen K (DK); Christina Christoffersen, Copenhagen K (DK); Victoria Blaho, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 89 days.

(21) Appl. No.: 14/122,057

(22) PCT Filed: May 23, 2012

(86) PCT No.: PCT/US2012/039142
§ 371 (c)(1),
(2), (4) Date: Jun. 20, 2014

(87) PCT Pub. No.: WO2012/162392
PCT Pub. Date: Nov. 29, 2012

(65) Prior Publication Data
US 2014/0303086 A1    Oct. 9, 2014

Related U.S. Application Data

(60) Provisional application No. 61/489,045, filed on May 23, 2011.

(51) Int. Cl.
| | | |
|---|---|---|
| *A61K 38/17* | (2006.01) | |
| *A61K 9/127* | (2006.01) | |
| *A61K 31/137* | (2006.01) | |
| *A61K 31/661* | (2006.01) | |
| *A61K 9/51* | (2006.01) | |

(52) U.S. Cl.
CPC ........ *A61K 38/1709* (2013.01); *A61K 31/137* (2013.01); *A61K 31/661* (2013.01); *A61K 9/127* (2013.01); *A61K 9/1275* (2013.01); *A61K 9/5123* (2013.01)

(58) Field of Classification Search
CPC .......... A61K 38/1709; A61K 47/48838; A61K 38/17; A61K 9/1275; C07K 14/775
See application file for complete search history.

(56) References Cited

U.S. PATENT DOCUMENTS

| | | |
|---|---|---|
| 7,250,407 B2 | 7/2007 | Dasseux et al. |
| 7,435,717 B2 | 10/2008 | Bisgaier et al. |
| 7,566,695 B2 | 7/2009 | Dasseux et al. |
| 7,994,120 B2 | 8/2011 | Dasseux et al. |
| 2004/0026666 A1 | 2/2004 | Chauvin et al. |
| 2008/0050351 A1 | 2/2008 | Dasseux et al. |
| 2008/0293633 A1 | 11/2008 | Bisgaier et al. |
| 2009/0130100 A1 | 5/2009 | Sabbadini et al. |
| 2010/0160259 A1 | 6/2010 | Schmouder et al. |
| 2011/0020242 A1 | 1/2011 | Zheng et al. |
| 2014/0171365 A1* | 6/2014 | Tall .................... A61K 38/1709 514/7.4 |

FOREIGN PATENT DOCUMENTS

| | | |
|---|---|---|
| WO | 2004/105773 A2 | 12/2004 |
| WO | 2009/056330 A1 | 5/2009 |
| WO | 2010/049103 A1 | 5/2010 |

OTHER PUBLICATIONS

Badimon et al., J Clin Invest. Apr. 1990; 85(4): 1234-1241.*
Sato et al., World J Biol Chem Nov. 26, 2010; 1(11): 327-337.*
Garcia, J.G. et al., "Sphingosine 1-Phosphate Promotes Endothelial Cell Barrier Integrity by Edg-Dependent Cytoskeletal Rearrangement" J. Clin. Invest. (Sep. 2001) pp. 689-701, vol. 108, No. 5.
Kimura, T. et al., "Role of Scavenger Receptor Class B Type I and Sphingosine 1-Phosphate Receptors in High Density Lipoprotein-Induced Inhibition of Adhesion Molecule Expression in Endothelial Cells" J. Biol Chem. (2006) pp. 37457-37467, vol. 281.
Aoki, S. et al., "Sphingosine 1-phosphate-related metabolism in the blood vessel" J.Biochem. (2005) pp. 47-55, vol. 138.
Nofer, J.R. et al., "HDL induces NO-dependent vasorelaxation via the lysophospholipid receptor S1P3" J. Clin. Invest. (2004) pp. 569-581, vol. 113.
Argraves, K.M. et al., "HDL serves as a S1P signaling platform mediating a multitude of cardiovascular effects" J. Lipid Res. (2007) pp. 2325-2333, vol. 48.
Ishii, I. et al., "Lysophospholipid receptors: Signaling and biology" Annu. Rev. Biochem. (2004) pp. 321-354, vol. 73.
Liu, Y. et al., "Edg-1, the G protein-coupled receptor for sphingosine-1-phosphate, is essential for vascular maturation" J. Clin. Invest. (2000) pp. 951-961, vol. 106.
Paik, J.H. et al., "Sphingosine 1-phosphate-induced endothelial cell migration requires the expression of EDG-1 and EDG-3 receptors and Rho-dependent activation of alpha vbeta3- and betal-containing integrins" J. Biol Chem. (2001) pp. 11830-11837, vol. 276.
Lee, M. J. et al., "Vascular endothelial cell adherens junction assembly and morphogenesis induced by sphingosine-1-phosphate" Cell (1999) pp. 301-312, vol. 99.
Camerer, E. et al., "Sphingosine-1-phosphate in the plasma compartment regulates basal and inflammation-induced vascular leak in mice" J. Clin Invest, (2009) pp. 1871-1879, vol. 119.
Pappu, R. et al., "Promotion of Lymphocyte Egress into Blood and Lymph by Distinct Sources of Sphingosine-1-Phosphate" Science (Apr. 13, 2007) pp. 295-298, vol. 316.

(Continued)

*Primary Examiner* — Daniel C Gamett
(74) *Attorney, Agent, or Firm* — Scully, Scott, Murphy & Presser, P.C.

(57) ABSTRACT

Apolipoprotein M forms a complex with sphingosine-1-phosphate (S1P) and is the carrier of S1P in high density lipoprotein particles and mediates its endothelial protective effect. Increasing the concentration of the apoM/S1P complex by administering it, either alone or in HDL particles, can prevent or treat diseases caused by endothelial cell injury, including inflammatory diseases, sepsis, atherosclerosis and acute lung injury, ischemic heart disease, stroke, vital organ failure after ischemic stress.

14 Claims, 12 Drawing Sheets

(56) References Cited

OTHER PUBLICATIONS

Venkataraman, K. et al., "Vascular endothelium as a contributor of plasma sphingosine 1-phosphate" Circ. Res. (2008) pp. 669-676, vol. 102.
Argraves, K.M. et al., "High density lipoprotein-associated sphingosine 1-phosphate promotes endothelial barrier function" J. Biol Chem. (2008) pp. 25074-25081, vol. 283.
Xu, N. et al., "A Novel Human Apolipoprotein (apoM)" J. Biol. Chem. (1999) pp. 31286-31290, vol. 274.
Christoffersen, C. et al., "The Signal Peptide Anchors Apolipoprotein M in Plasma Lipoprotein and Prevents Rapid Clearance of Apolipoprotein M from Plasma" Journal of Biological Chemistry (Jul. 4, 2008) pp. 18765-18772, vol. 283, No. 27.
Christoffersen, C. et al., "Isolation and Charachterization of Human Apolipoprotein M-containing Lipoproteins" Journal of Lipid Research (2006) pp. 1833-1843, vol. 47.
Christoffersen, C. et al., "Effect of Apolpoprotein M on High Density Lioprotein Metabolism and Atherosclerosis in Low Density Lipoprotein Receptor Knock-out Mice" Journal of Biological Chemistry (Jan. 25, 2008) pp. 1839-1847, vol. 283, No. 4.
Wolfrum, C. et al., "Stoffel M. Apolipoprotein M is required for prebeta-HDL formation and cholesterol efflux to HDL and protects against atherosclerosis" Nat. Med. (Apr. 2005) pp. 418-422, vol. 11, No. 4.
Sevvana, M. et al., "Serendipitous Fatty Acid Binding Reveals the Structural Determinants for Ligand Recognition in Apolipoprotein M" J.Mol.Biol. (2009) pp. 920-936, vol. 393.
Liu, C.H. et al., "Ligand-induced trafficking of the sphingosine-1-phosphate receptor EDG-1" Mol. Biol Cell (1990) pp. 1179-1190, vol. 10.
Oo, M.L. et al., "Immunosuppressive and anti-angiogenic sphingosine 1-phosphate receptor-1 agonists induce ubiquitinylation and proteasomal degradation of the receptor" J. Biol. Chem. (2007) pp. 9082-9089, vol. 282.
Awad, A.S. et al., "Selective sphingosine 1-phosphate 1 receptor activation reduces ischemia-reperfusion injury in mouse kidney" Am J Physiol Renal Physiol. (2006) pp. F1516-F1524, vol. 290.
Christoffersen, C. et al., "Opposing effects of apolipoprotein m on catabolism of apolipoprotein B-containing lipoproteins and atherosclerosis" Circ. Res. (2010) pp. 1624-1634, vol. 106.
He, X. et al., "Quantitative analysis of sphingosine-1-phosphate by HPLC after napthalene-2,3-dicarboxaldehyde (NDA) derivatization" J. Chromatogr. B Analyt. Technol. Biomed. Life Sci (2009) pp. 983-990, vol. 877.
Bielawski, J. et al., "Comprehensive quantitative analysis of bioactive sphingolipids by high-performance liquid chromatography-tandem mass spectrometry" Methods Mol. Biol. (2009) pp. 443-467, vol. 579.
Hla, T. et al., "An abundant transcript induced in differentiating human endothelial cells encodes a polypeptide with structural similarities to G-protein-coupled receptors" J. Biol. Chem.(1990) pp. 9308-9313, vol. 265.
Michaud, J. et al., "Inhibitory role of sphingosine 1-phosphate receptor 2 in macrophage recruitment during inflammation" J. Immunol. (2010) pp. 1475-1483, vol. 184.
Bricarello, D.A. et al., "Reconstitued Lioprotein: A Versatile Class of Biologically-Inspired Nanostructures" ACS Nano (2011) pp. 42-57, vol. 5, No. 1.
Lee, M.J. et al., "Sphingosine-1-Phosphate as a Ligand for the G Protein-Coupled Receptor EDG-1" Science (1998) pp. 1552-1555, vol. 279.
Katzen, F. et al., "Insertion of Membrane Proteins into Discoidal Membranes Using a Cell-Free Protein Expression Approach" Journal of Proteome Research (2008) pp. 3535-3542, vol. 7, No. 8.
Pham et al., "Lymphatic endothelial cell sphingosine kinase activity is required for lymphocyte egress and lymphatic patterning" J. Exp. Med (2010) pp. 17-27, vol. 207.
Christoffersen, C. et al., "Endothelium-Protective Sphingosine-1-Phosphate Provided by HDL-Associated Apolipoprotein M" PNAS (Jun. 7, 2011) pp. 9613-9618, vol. 108, No. 23.
International Search Report dated Aug. 23, 2012 issued in International Application No. PCT/US2012/039142.
Karuna, R. et al., "Plasma Levels of Sphingosine-1-Phosphate and Apolipoprotein M in Patients with Monogenic Disorders of HDL Metabolism" Atherosclerosis (2011) pp. 855-863, vol. 219.
Huang, X.S. et al., "Apolipoprotein M likely Extends its Anti-Atherogenesis via Anti-Inflammation" Medical Hypotheses (2007) pp. 136-140, vol. 69.
Christoffersen, C. et al., "Apolipoprotein M—a New Biomarker in Sepsis" Critical Care (May 17, 2012) pp. 126-127, vol. 16, No. 3.
Ahnström, J. et al., "HDL Stimulates apoM Secretion" Protein & Peptide Letters (2010) pp. 1-5, vol. 17, No. 10.
Chiesa, G. et al., "Acute Effects of High-Density Lipoproteins: Biochemical Basis and Clinical Findings" Current Opinion in Cardiology (2008) pp. 379-385, vol. 23.

* cited by examiner

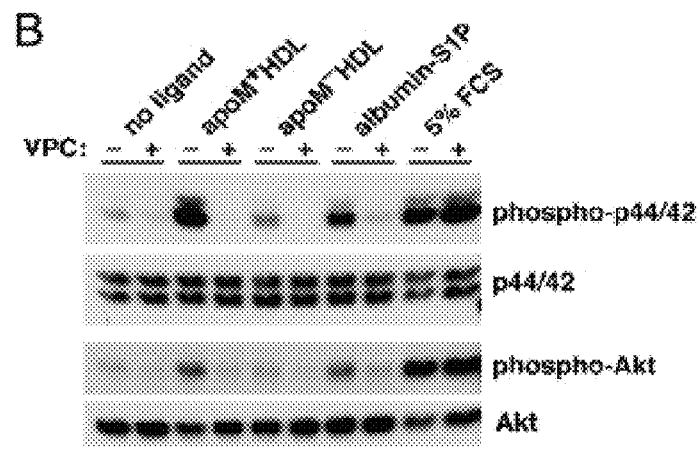
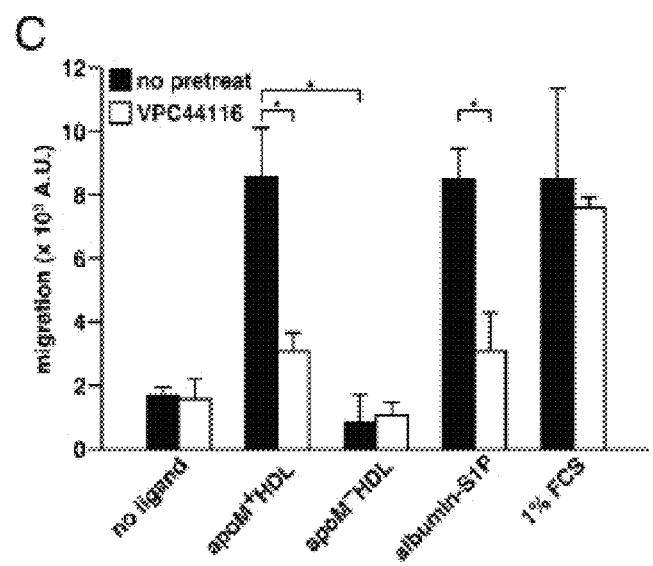
Figures 4B-C

ENDOTHELIUM PROTECTIVE MATERIALS AND METHODS OF USE

CROSS REFERENCE TO RELATED APPLICATION

This application claims priority from U.S. Provisional Application No. 61/489,045, filed May 23, 2011, the entire contents of which are incorporated herein by reference.

STATEMENT REGARDING FEDERALLY SPONSORED RESEARCH OR DEVELOPMENT

This invention was made with Government support under Grant Number HL-67330, HL-70694 and HL89934 awarded by the National Institutes of Health. The United States Government has certain rights in the invention.

INCORPORATION BY REFERENCE OF SEQUENCE LISTING

The Sequence Listing in an ASCII text file, named as 27646_5429_03_SequenceListing.txt of 4 KB, created on Nov. 22, 2013, and submitted to the United States Patent and Trademark Office via EFS-Web, is incorporated herein by reference.

FIELD OF THE DISCLOSURE

This invention relates to endothelial protective compositions and use thereof in the prevention and treatment of conditions associated with endothelial cell injury. In particular, the compositions contain apolipoprotein M (apoM), optionally complexed with sphingosine-1-phosphate (S1P), either alone or in HDL particles or reconstituted nanolipostructures.

BACKGROUND ART

Sphingosine-1-phosphate (S1P), the phosphorylated metabolite of D-sphingosine, binds to five G protein-coupled receptors (S1P1-S1P5) and regulates a plethora of biological actions (GARCIA et al., J. Clin. Invest, 108:689-701 (2001); ISHII et al., Annu. Rev. Biochem., 73:321-354 (2004)). In particular, the prototypical S1P1 receptor is essential for vascular maturation during development and promotes endothelial cell migration, angiogenesis and barrier functions (LIU et al., J. Clin. Invest, 106:951-961 (2000); PAIK et al., J. Biol Chem., 276:11830-11837 (2001); LEE et al., Cell, 99:301-312 (1999)). Thus, S1P is required for maintenance of the barrier property of the lung endothelium (CAMERER et al., J. Clin. Invest, 119:1871-1879 (2009)). Plasma S1P, which is derived from several cellular sources (PAPPU et al., Science, 316:295-298 (2007); VENKATARAMAN et al., Circ. Res., 102:669-676 (2008)), is associated with high density lipoprotein (HDL) (~65%) and albumin (~35%) (AOKI et al., J. Biochem., 138:47-55 (2005); ARGRAVES et al., J. Lipid Res., 48:2325-2333 (2007)). HDL-induced vasorelaxation as well as barrier-promoting and pro-survival actions on the endothelium have been attributed to S1P signalling (KIMURA et al., J. Biol Chem., 281:37457-37467 (2006); NOFER et al., J. Clin. Invest, 113:569-581 (2004); ARGRAVES et al., J. Biol Chem., 283:25074-25081 (2008)). Hence, much of the endothelium-protective actions of HDL may be due to the actions of S1P on the endothelial S1P receptors. The molecular nature of the S1P binding to HDL and interaction to S1P receptors, however, has not been characterized. The molecular structure of S1P is displayed in FIG. 6.

Apolipoprotein M (apoM) is a ~22-kDa HDL-associated apolipoprotein and a member of the lipocalin family of proteins which mainly resides in the plasma HDL fraction (XU et al., J. Biol Chem., 274:31286-31290 (1999)). Mature apoM (human apoM, SEQ ID NO: 1, and murine apoM, SEQ ID NO: 2) retains its signal peptide, which serves as a lipid anchor attaching apoM to the phospholipid layer of the lipoproteins, thereby keeping it in the circulation and preventing filtration of apoM in the kidney (CHRISTOFFERSEN et al., J. Biol Chem., 283:18765-18772 (2008)). The biological functions of apoM are only partly understood and the mechanisms by which it enables these functions are unknown. Studies in apoM gene-modified mice suggest that apoM has antiatherogenic effects, possibly related in part to the ability of apoM to increase cholesterol efflux from macrophage-foam cells, to increased preβ-HDL formation and to anti-oxidative effects (CHRISTOFFERSEN et al., J. Lipid Res., 47:1833-1843 (2006); CHRISTOFFERSEN et al., J. Biol Chem., 283:1839-1847 (2008); WOLFRUM et al., Nat. Med., 11:418-422 (2005)). The recent elucidation of the crystal structure of recombinant human apoM demonstrated a typical lipocalin fold characterized by an eight-stranded antiparallel β barrel that encloses an internal binding pocket, which likely facilitates binding of small lipophilic ligands (SEVVANA et al., J. Mol. Biol, 393:920-936 (2009)). Indeed, the recombinant apoM, which was expressed in E. coli, was found to cocrystallize with myristic acid (SEVVANA et al., J. Mol. Biol, 393:920-936 (2009)). This illustrated that apoM can bind lipid compounds with fatty acid side chains, and in vitro binding experiments demonstrated that S1P displaced the myristic acid with an IC50 of 0.90 μM (SEVVANA et al., J. Mol. Biol, 393:920-936 (2009)).

SUMMARY OF THE DISCLOSURE

This invention is directed to compositions and use thereof in the prevention and treatment of conditions associated with endothelial cell injury, and in the treatment of autoimmune disorders. The invention stems from the discovery that Apolipoprotein M forms a complex with sphingosine-1-phosphate (S1P) and is the carrier of S1P in high density lipoprotein particles and mediates its endothelial protective effect.

In one aspect, this invention provides a method of treating or reducing the risk of developing a disease associated with endothelial injury in a subject, based on administration of a therapeutically effective amount of a composition comprising ApoM. In some embodiments, the ApoM protein is recombinantly produced. In specific embodiments, the ApoM protein is incorporated in a HDL-like nanostructure. In particular embodiments, the ApoM is complexed with S1P. In other embodiments, the composition comprising ApoM is composed of ApoM-containing HDLs isolated from human plasma.

Diseases associated with endothelial injury include, but are not limited to, atherosclerosis, ischemic cardiovascular disease, stroke, vital organ failure after ischemic stress, ischemic peripheral vascular disease, peripheral vascular disorders associated with diabetes, vascular leak syndrome, autoimmune vasculitis, adult (acute) respiratory distress syndrome, acute lung injury, ventilator-induced pneumonia, Dengue hemorrhagic fever, SARs, influenza, swine flu, thrombocytopenia, hemangioma, inflammatory diseases, malaria, sickle cell anemia, dialysis-induced vascular injury, diabetic retinopathy, wet age-related macular degeneration and sepsis.

In another aspect, the invention provides a method of treating an autoimmune disorder in a subject based on administration of a compound which inhibits the formation or function of the ApoM/S1P complex in the subject.

In still another aspect, the invention provides a method of reducing a side effect of Fingolimod in a patient being treated with Fingolimod for an autoimmune disorder, by administering ApoM to the patient.

Autoimmune disorders contemplated by this invention include, for example, multiple sclerosis, psoriasis, rheumatoid arthritis, uveitis and type I diabetes.

In a further aspect, this invention provides a composition comprising an isolated ApoM/S1P complex.

In another aspect, the invention provides reconstituted HDL-like nanostructures integrated with ApoM, optionally complexed with S1P.

DETAILED DESCRIPTION

Figures 1A, 1B, 1C:
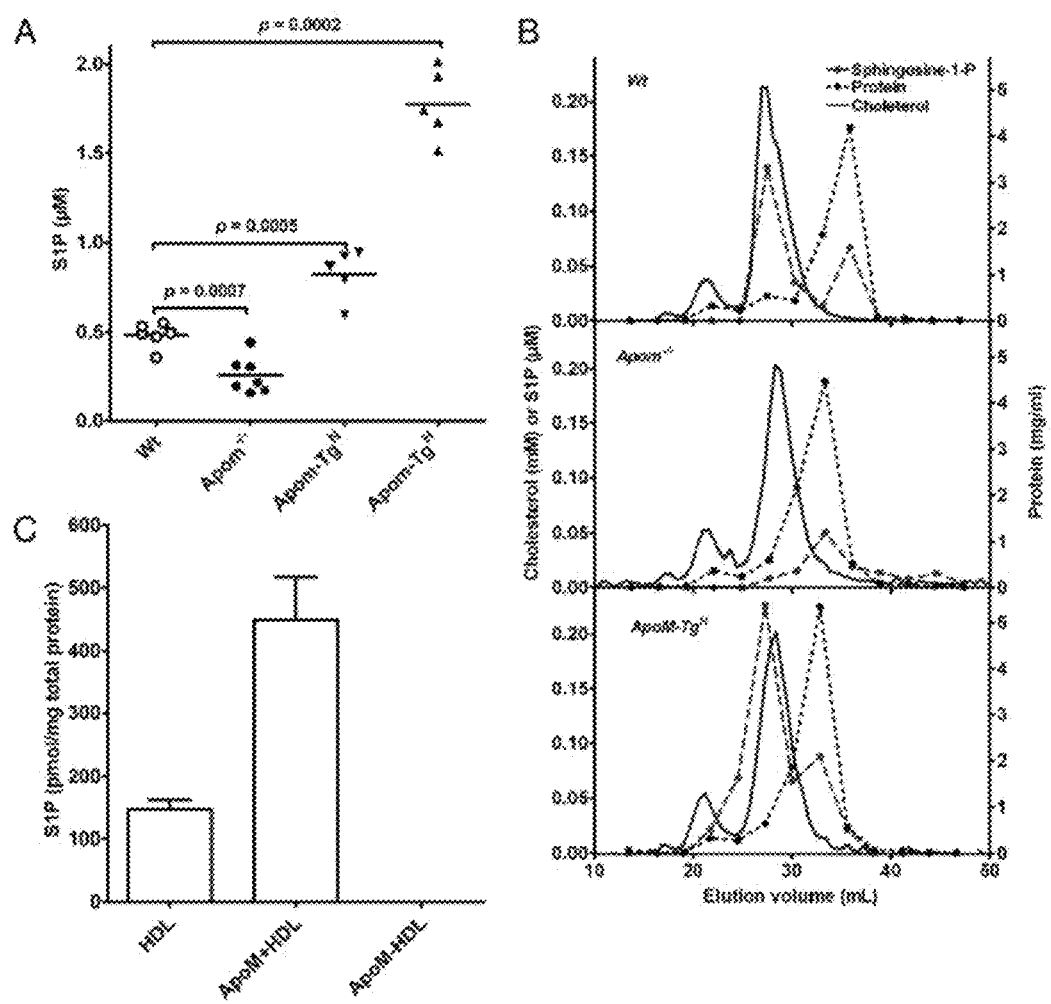
FIG. 1. ApoM gene dosage determines plasma S1P in genetically modified mice. (A) Plasma S1P in Wt, $Apom^{-/-}$, and apoM-transgenic female mice with ~2-fold ($Apom-Tg^N$) and ~10-fold ($Apom-Tg^H$) increased plasma apoM. Each point represents data from an individual mouse, lines indicate means. (B) Lipoproteins in pools of plasma from Wt (top), $Apom^{-/-}$, (middle) or $Apom-Tg^H$ mice were separated by gel filtration on serially connected Superose 6 and 12 columns. The flow rate was 0.4 ml/min, fractions of 275 µl were collected. Aliquots of 10 consecutive fractions were pooled prior to measuring S1P (red filled symbols) and protein (dotted black line). Cholesterol concentration (full blue line) was determined in each fraction. The scale bar for cholesterol (mmol/l) and S1P (µmol/l) is shown on the left y-axis. Protein (mg/ml) is shown on the right y-axis. C) S1P was measured with HPLC in purified preparations of human total HDL, $apoM^+HDL$ and $apoM^-HDL$. Values are mean±SEM, n=3. N.D.=not detectable. Results were confirmed by LC-MS/MS.

It has been identified in accordance with the present invention that Apolipoprotein M (ApoM) is the carrier of S1P in high density lipoprotein (HDL) particles and mediates the biological effects of S1P, including its protective effects on endothelial cells and regulation of the egress of T and B cells from secondary lymphoid organs. Increasing the concentration of the apoM/S1P complex in a subject by administering apoM, alone or in complex with S1P, optionally in HDL particles or reconstituted nanolipostructures, can prevent or treat conditions associated with endothelial cell injury. Further, regulating the apoM/S1P system is also beneficial to the treatment of autoimmune disorders. Pharmaceutical compositions containing apoM and the related therapeutic methods are further disclosed herein below.

By "conditions associated with endothelial cell injury" it is meant conditions or disorders that are characterized by endothelial cell injury. Endothelial injury can be caused by hypertension, stress-induced hormones, chemical toxins, pollution, cholesterol, infectious agents (e.g., *Chlamydia pneumoniae, Helicobacter pylori, Candida albicans*, viruses such as herpesviruses, Dengue virus that causes hemorrhagic fever), and various diseases including infectious diseases that cause tissue edema by inducing vascular permeability. Endothelial cell injury can be, but is not necessarily the direct or only cause for the condition or disorder being targeted by administration of an ApoM-containing composition in this application. In some embodiments, conditions associated with endothelial cell injury display compromised vascular integrity or increased vascular permeability.

Conditions associated with endothelial cell injury include, but are not limited to atherosclerosis, ischemic cardiovascular disease (such as ischemic heart disease), stroke, vital organ (e.g., kidney, liver, intestine) failure after ischemic stress, ischemic peripheral vascular disease, peripheral vascular disorders associated with diabetes, vascular leak syndrome, autoimmune vasculitis, adult (acute) respiratory distress syndrome, acute lung injury, ventilator-induced pneumonia, dialysis-induced vascular injury, Dengue hemorrhagic fever, malaria, sickle cell anemia, SARs, influenza, swine flu, thrombocytopenia, hemangioma, inflammatory diseases, diabetic retinopathy, wet age-related macular degeneration, and sepsis. Examples of inflammatory diseases suitable for treatment herein include systemic lupus erythromatosus, in which vascular endothelial cell injury is implicated in disease progression, and systemic inflammatory response syndrome (SIRS), which appears to be a sepsis-like condition without an infection and can be caused by trauma, burns, pancreatitis, ischemia, and hemorrhage.

In some embodiments, an ApoM-containing pharmaceutical composition can be administered to a patient for preventing or reducing the likelihood of developing a condition associated with endothelial cell injury, especially a patient at risk of developing such a condition. In other embodiments, an ApoM-containing pharmaceutical composition is administered to a patient suffering from a condition associated with endothelial cell injury.

In some embodiments, a pharmaceutical composition suitable for therapeutic use herein contains recombinantly produced ApoM protein. The human ApoM gene is available, and the protein sequence is set forth in SEQ ID NO: 1, with the first twenty one (21) amino acids representing a signal peptide.

In one embodiment, soluble recombinant ApoM protein, with or without the signal peptide, can be produced in an appropriate cell-based expression system, such as a bacterial or eukaryotic cell expression system. For example, human ApoM protein can be expressed in *E. coli*, recovered from inclusion bodies, purified (e.g., through chromatography), and refolded, as described by SEVVANA et al., *J. Mol. Biol.* 393: 920-936 (2009).

In another embodiment, recombinant ApoM protein is produced using an in vitro cell-free translation system, available commercially e.g., through Life Technology or any other appropriate source. Both prokaryotic and eukaryotic cell-free translation systems can be used. Typically, a cell-free translation system utilizes extracts prepared from cells engaged in a high rate of protein synthesis, such as rabbit reticulocytes, wheat germ and *E. coli*, which contain the macromolecular components (70S or 80S ribosomes, tRNAs, aminoacyl-tRNA synthetases, initiation, elongation and termination factors, for example) required for translation. The extract is generally supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors (Mg2+, K+, etc.). Some translation systems, such as reticulocyte lysates and wheat germ extracts, use RNA as a template, whereas other systems start with DNA templates, which are transcribed into RNA then translated. All these systems are suitable for use in synthesis of an ApoM protein in vitro.

In a specific embodiment, a recombinant ApoM protein is incorporated into HDL-like nanostructures (referred to herein as reconstituted or synthetic nanoparticles or nanodiscs).

By "HDL-like nanostructures" it is meant herein reconstituted and synthetic nanostructures that are similar to native HDL in terms of size and composition. Native biological HDLs exist as discoidal lipid bilayer of 5-8 nm diameter and lipid monolayer-coated spheres 10-15 nm in diameter. Reconstituted HDL-like nanostructures generally are of a dimension of 5-15 nm in diameter, and can be in the form of 5-15 nm or 5-8 nm nanodiscs, or the form of 5-15 nm of 10-15 nm nanospheres.

HDL-like nanodiscs can be reconstituted by adding lipid-free apolipoprotein(s) to phospholipid vesicles and incubating under appropriate reaction conditions that allow the formation of lipoprotein structures. See, e.g., BRICARELLO et al., *ACS NANO* 5(1): 42-57 (2010); U.S. Published Application 2004/026666A1. Appropriate reaction conditions include, e.g., the initial presence of a detergent (e.g., sodium cholate) and subsequent removal (e.g., dialysis) of the detergent. See, supra. In specific embodiments disclosed herein, apolipoprotein A, which is the principal apolioprotein component of native HDLs, is used in forming reconstituted HDLs. The phospholipid component of the reconstituted HDL nanostructures can be one type of phospholipid, or a mixture of two or more different types. The phospholipids can be varied based on their head group, which can be chosen from those typically found in native HDLs, including phosphatidyl serine, phosphatidylinositol, phosphatidyl ethanolamine and sphingomyelin; as well as chosen from other useful head groups including phosphatidyl glycerol, phosphatidyl serine, phosphatidyl inositol, phosphatidyl ethanolamine, cerebroside or a ganglioside. The fatty acyl substituents of phospholipids of reconstituted HDLs herein can also be varied. Examples of fatty acid substituents of phospholipids include 1-palmitoyl-2-oleoyl-, 1-palmitoyl-2-linoleoyl-, 1-palmitoly-2-arachadonyl-, 1-palmitoyl-2-docosahexanoyl. Additional fatty acyl groups can also be chosen to provide desirable characteristics, e.g., fatty acyl groups having acyl chains of about 12 to about 18 carbon atoms.

In one example, HDL-like nanostructures are formed by incubating a mixture of ApoA1, 1,2-dimyristoyl-sn-glycero-3-phosphocholine, and cholate. Cholate is then removed by incubating with nonpolar polystyrene beads, and the nanostructures (formed by ApoA1 and phosphocholine) can be purified by chromotography (e.g., size exclusion chromatography).

Incorporation of ApoM into HDL-like nanostructures can be achieved by producing ApoM protein in an in vitro cell-free translation system in the presence of assembled HDL-like nanostructures, or in the presence of the components needed for the assembly of HDL-like nanostructures (e.g., ApoA1 and phospholipids). Alternatively, recombinantly produced ApoM proteins can be mixed with the components (e.g., ApoA1 and phospholipids), and the mixture is subject to the reconstitution process described above.

In other embodiments, a pharmaceutical composition suitable for therapeutic use is composed of substantially purified native HDLs containing ApoM proteins. Such ApoM-containing HDLs can be purified from human plasma as described, e.g., by CHRISTOFFERSEN et al., *J. Lipid Res.* 47: 1833-1843 (2006).

In some embodiments, ApoM is allowed to form a complex with S1P prior to therapeutic use. Soluble isolated ApoM proteins, or alternatively, HDL-like nanostructures containing ApoM proteins, can be incubated with S1P to allow the formation of the ApoM-S1P complex. See, e.g., LEE et al., *Science,* 279:1552-1555 (1998). As used herein, an "isolated ApoM/S1P complex" refers to an complex of ApoM and S1P in an isolated, substantially purified form, i.e., substantially free from lipids typically observed in native HDLs or used in reconstituted HDLs.

In other embodiments, an ApoM pharmaceutical composition is administered without S1P, and recruits and forms complex with circulating S1P in the recipient after administration. Plasma S1P is derived from several cellular sources (PAPPU et al., *Science* 316: 295-298, 2007). For example, S1P is stored in relatively high concentrations in human platelets, which lack the enzymes responsible for its catabolism, and is released into the blood stream upon activation of physiological stimuli, such as growth factors, cytokines, and receptor agonists and antigens.

ApoM-containing pharmaceutical compositions described above can include additional pharmacological agents appropriate for use in the treatment of disorders associated with endothelial cell injury or autoimmune disorders. Suitable additional pharmacological agents include, for example, cytotoxic agents, chemotherapeutic agents, hormones, steroidal anti-inflammatory drugs (e.g., prednisone, corticosteroids, and the like), non-steroidal anti-inflammatory drugs (e.g., NSAIDs, aspirin, acetaminophen, and the lice); and combinations thereof.

Pharmaceutical compositions may be prepared using one or more physiologically acceptable carriers or excipients. As used herein, a pharmaceutically acceptable carrier includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof. In some embodiments, the carrier is a controlled release matrix, a material which allows the slow release of the active ingredients in ApoM-containing compositions.

In accordance with the present invention, the active ingredients of the present pharmaceutical compositions can be combined with a carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. When appropriate, the pharmaceutical compositions of the present invention should be made sterile by well known procedures. For example, solutions can be made sterile by filter sterilization or autoclave. To obtain a sterile powder, sterilized solutions can be vacuum-dried or freeze-dried as necessary.

The pharmaceutical compositions of the present invention can be administered to a subject by standard routes, including the oral, nasal, intratracheal, transdermal, parenteral (e.g., intravenous, intraperitoneal, intradermal, subcutaneous or intramuscular) or rectal route. In addition, an ApoM-containing composition can be introduced into the body, by injection or by surgical implantation or attachment, proximate to a preselected tissue or organ site such that a significant amount of the active ingredients is able to enter the site, e.g., in a controlled release fashion, by direct diffusion.

The dosage depends on the disease state or condition being treated and other clinical factors, such as weight and condition of the subject, the subject's response to the therapy, the type of formulations and the route of administration. The precise dosage to be therapeutically effective and non-detrimental can be determined by those skilled in the art. Generally speaking, a pharmaceutical composition can be administered at about 0.5 μg to about 2 grams per unit dosage form. A unit dosage form refers to physically discrete units suited as unitary dosages for mammalian treatment: each unit containing a pre-determined quantity of the active material calculated to produce the desired therapeutic effect in association with any required pharmaceutical carrier. The methods of the present invention contemplate single as well as multiple administrations, given either simultaneously or over an extended period of time.

In a further aspect, the apoM/S1P system is manipulated to facilitate the treatment of autoimmune disorders. Autoimmune disorders suitable for treatment in accordance with this invention include, for example, multiple sclerosis, psoriasis, rheumatoid arthritis, uveitis, and type I diabetes.

In one embodiment, a compound that specifically inhibits the formation or function of apoM/S1P is administered to a patient suffering from an autoimmune disorder in order to ameliorate the symptoms or retard the progression of the disorder. Compounds that have been previously identified as S1P or S1P1 inhibitors (such as FTY720/Fingolimod/Gilenya™) are excluded from this aspect of the invention. Suitable compound inhibitors can be identified by, for example, screening combinatorial libraries based on any of the assays described herein including the migration assay, the vascular permeability assay, the $S1P_1$ receptor internalization assay, and the adherens junction assembly assays, described in Example 3. Further, antibodies against ApoM may also be used to inhibit ApoM/S1P function in autoimmune disorders.

In another embodiment, an isolated apoM protein is given to a patient undergoing a treatment with FTY720/Fingolimod/Gilenya™ (IUPAC name: 2-amino-2-[2-(4-octylphenyl)ethyl]propane-1,3-diol) or analogs thereof for an autoimmune disorder. FTY720/Fingolimod/Gilenya™ is an approved therapeutic for multiple sclerosis and may be useful for treating other autoimmune indications such as psoriasis, rheumatoid arthritis, uveitis and type I diabetes. The most common side effects of fingolimod have been head colds, headache, and fatigue. However, Fingolimod has been associated with potentially fatal infections, bradycardia, skin cancer, and a case of hemorrhaging focal encephalitis, an inflammation of the brain with bleeding. In accordance with this invention, it is believed that the side effects of Fingolimod and its analogs can be reduced by the administered apoM, which will sequester the excess circulating S1P molecules.

The present description is further illustrated by the following examples, which should not be construed as limiting in any way. The contents of all cited references (including literature references, issued patents, and published patent applications as cited throughout this application) are hereby expressly incorporated by reference.

Example 1

Apo M is the Physiological Carrier of S1P

To elucidate whether apoM is the physiological carrier of HDL-associated S1P in vivo, plasma S1P was measured in apoM knockout (Apom$^{-/-}$) mice and in two lines of human apoM transgenic mice, having either 2-fold (Apom-Tg$^N$) or 10-fold (Apom-Tg$^H$) increased plasma apoM concentrations (CHRISTOFFERSEN et al., J. Biol Chem., 283:1839-1847 (2008)).

Mice. Mice were housed at the Panum Institute, University of Copenhagen, Copenhagen, and fed standard chow (Altromin1314). Apom-Tg$^N$, Apom-Tg$^H$, or Apom$^{-/-}$ female mice were backcrossed more than seven times with C57B6/J mice (CHRISTOFFERSEN et al., J. Biol Chem., 283:1839-1847 (2008), CHRISTOFFERSEN et al., Circ. Res., 106:1624-1634 (2010)). WT mice were Apom-Tg littermates. Blood taken from the orbital venous plexus was placed in tubes containing ethylenediaminetetraacetic acid, kept on ice until plasma was isolated, and frozen in N$_2$ before storage at −80° C. All procedures were approved by the Animal Experiments Inspectorate, Ministry of Justice, Denmark.

Lipoproteins and S1P. Human apoM$^+$HDL and apoM$^-$HDL were isolated from human plasma with ultracentrifugation (1.063-1.21 g/l) followed by immuno-affinity chromatography on an anti-apoM monoclonal column (CHRISTOFFERSEN et al., J. Lipid Res., 47:1833-1843 (2006)). ApoM was quantified with ELISA (26). For gel filtration, plasma samples (500 µl) from Apom-Tg$^H$ (n=5), Apom$^{-/-}$ (n=7) and Wt (n=6) were separated on serially connected Superose 6 and Superose 12 10/300 GL columns (CHRISTOFFERSEN et al., J. Lipid Res., 47:1833-1843 (2006)). S1P was measured with HPLC (HE et al., J. Chromatogr. B Analyt. Technol. Biomed. Life Sci, 877:983-990 (2009)) or LC-MS/MS (BIELAWSKI et al., Methods Mol. Biol, 579:443-467 (2009)). For HPLC based quantification of sphingosine-1-phosphate (S1P), plasma (25 µL), isolated human HDL fractions (150 µL), or gel filtration fractions (500 µL) were supplemented with 25 ng of an internal standard [D-erythro-sphingosine-1-phosphate (C17 base), Avanti; iNstruchemie]. The S1P-containing phase was isolated with chloroform-methanol extractions in a two-step procedure followed by derivatization with 2,3-naphthalenedicarboxaldehyde. One microliter of the derivatized sample was analyzed with an Agilent 1290 HPLC (Agilent Technologies) using a Synergi 4u Fusion-RP 80A column (30×2.0 mm; Phenomenex) with a flow of 0.5 mL/min. Separation was performed using a gradient of the mobile phase: 0-6 min, 47.5%; 6-9 min, 47.5-87.5%; 9-10 min, 87.5%; 10-12, min 87.5-47.5%; and 12-15 min, 47.5%. The mobile phase consisted of acetonitrile (HPLC grade; Rathburn Chemicals Ltd), and the aqueous phase consisted of 20 mM potassium phosphate (KH2PO4, pH 4.8, HPLC grade; Sigma-Aldrich), each supplemented with 15% methanol (HPLC grade; Sigma-Aldrich). Results were confirmed with an independent HPLC method and by liquid chromatography-tandem MS (BIELAWSKI et al., Methods Mol. Biol, 579:443-467 (2009)).

Figures 2A, 2B, 2C:
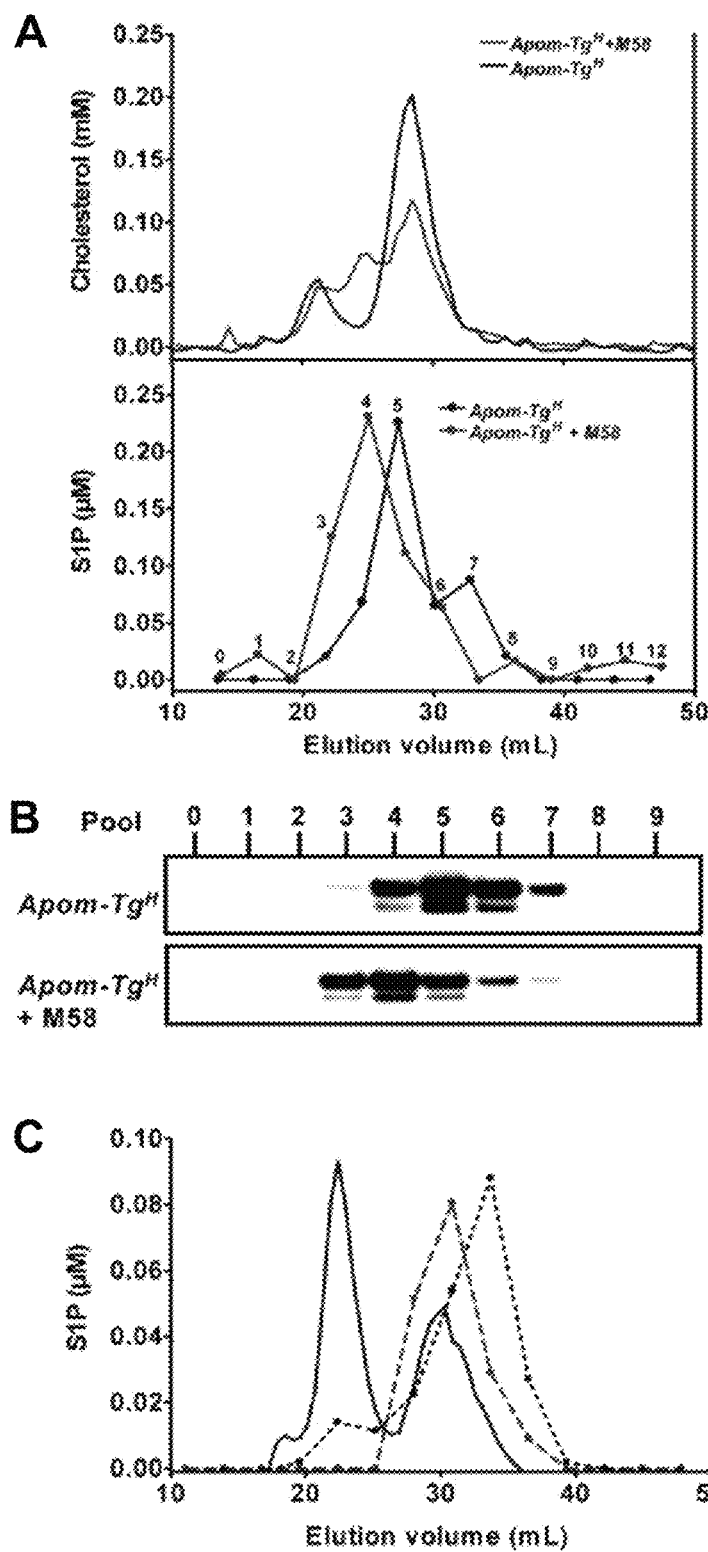
FIG. 2. S1P is bound in human apoM-containing HDL in ApoM-transgenic mice. Plasma from ApoM-TgH mice was analyzed directly or incubated with 600 µg of a monoclonal antibody against human apoM (M58) before gel filtration analysis as described in the legend for FIG. 1. (A) Cholesterol profiles of $Apom-Tg^H$ plasma with (unbroken line) or without (red line) preincubation with M58. Note the M58-induced increase in the size of cholesterol-containing HDL particles. S1P was determined in the gel filtration pools indicated. (B) Consecutive gel filtration fractions were collected in pools, and human apoM was visualized with Western blotting. Note the M58-induced increase in the size of the particles containing human apoM after preincubation with M58. (C) A pool of human plasma from 10 healthy individuals was subjected to gel filtration on serially connected Superose 6 and 12 columns. The flow rate was 0.4 mL/min. Fractions of 275 µL were collected. Aliquots of 10 consecutive fractions were pooled before measuring S1P (filled red symbols) and protein (dotted black line). Cholesterol concentration (solid blue line) was determined in each fraction. S1P eluted mainly in HDL- and albumin-containing fractions but not in LDL-containing fractions. The recovery of S1P was 108%.

As compared to wildtype (Wt) mice, plasma S1P was reduced 46% in Apom$^{-/-}$ mice (P=0.0007), and increased 71% (P=0.0005) and 267% (P=0.0002) in the Apom-Tg$^N$ and Apom-Tg$^H$ mice, respectively (FIG. 1A). The plasma concentrations of HDL-cholesterol, total phospholipids, and apoA-I were only marginally affected in Apom$^{-/-}$ and Apom-Tg$^H$ mice, demonstrating that the changes in S1P concentrations were related to apoM and not to variations in amount of circulating HDL (CHRISTOFFERSEN et al., J. Biol Chem., 283:1839-1847 (2008)). When lipoproteins in Wt mouse plasma were separated by gel filtration, the major peak of S1P co-eluted with apoM in the HDL fractions, whereas a minor S1P peak co-eluted with albumin (FIG. 1B). Apom$^{-/-}$ mice lacked S1P in the HDL fraction, but the S1P peak in the albumin fractions was present (FIG. 1B). Apom-Tg$^H$ mice had increased S1P in HDL (FIG. 1B). This S1P was associated with apoM-containing HDL, as demonstrated by a parallel shift in S1P- and human-apoM-elution profiles after the addition of a specific monoclonal antibody against human apoM (M58) to the plasma prior to gel filtration (FIG. 2A-B).

Importantly, the amount of apoM in HDL is sufficient to accommodate and account for all HDL-bound S1P. The average plasma apoM concentration is similar in mice and humans, i.e. ~0.9 µmol/l (CHRISTOFFERSEN et al., J. Biol Chem., 283:1839-1847 (2008)). Hence, the apparent molar ratio between HDL bound S1P and plasma apoM is ~1:3 in Wt and Apom-Tg$^N$ and ~1:6 in Apom-Tg$^H$ mice. On gel filtration of human plasma, the majority of S1P co-eluted with HDL indicating that also in humans the main part of lipoprotein-bound S1P is associated with HDL (FIG. 2C). When human HDL was separated by affinity chromatography into apoM$^+$HDL and apoM$^-$HDL fractions, S1P was exclusively found in apoM⁺HDL (FIG. 1C). These data indicate that S1P in HDL is bound to apoM in both humans and mice.

Example 2

Binding of S1P to Recombinant Mouse ApoM

Figure 3:
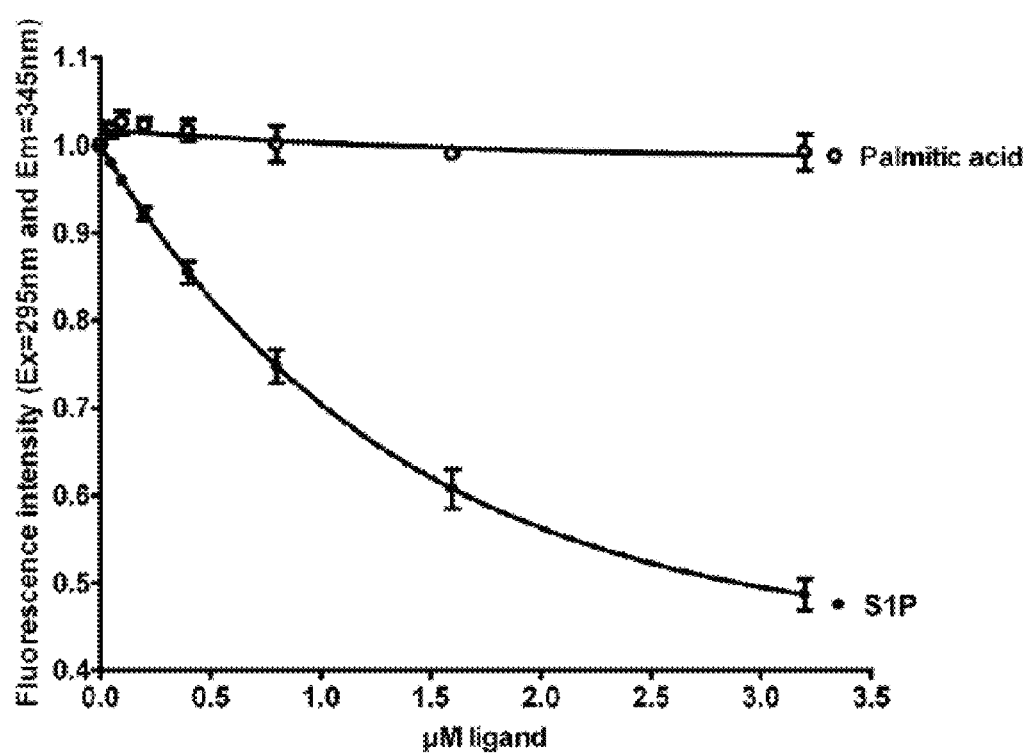
FIG. 3. S1P quenches the intrinsic fluorescence of mouse r-apoM. A truncated mouse r-apoM containing the lipocalin domain but lacking the hydrophobic signal peptide was produced in *Escherichia coli*. The r-apoM (0.7 µM) was incubated with increasing concentrations of S1P (final concentration: 0-3.2 µmol/L). The intrinsic fluorescence of apoM was measured with excitation at 295 nm and emission at 345 nm. The data are mean±SEM (n=3).

Intrinsic fluorescence quenching was studied after addition of S1P to 0.7 μM murine recombinant apoM (r-apoM) (SEVVANA et al., *J. Mol. Biol*, 393:920-936 (2009)). Because it is possible that murine r-apoM binds and contains myristic acid in a manner similar to that of its human counterpart (SEVVANA et al., *J. Mol. Biol*, 393:920-936 (2009)), the binding data are reported as IC50 values. This approach also allows S1P binding to murine r-apoM to be compared directly with the previous data on human apoM-S1P binding. The data are shown in FIG. 3.

Example 3

S1P Effects are Mediated by ApoM/S1P Complex

This Example describes experiments undertaken to test whether the apoM/S1P complex exhibited any of the physiological effects of S1P. These included migration assays, vascular permeability studies, assays related to $S1P_1$ receptor internalization and activation and adherens junction assembly assays.

General Methods. R-apoM- and Albumin-Bound S1P. S1P was dissolved in methanol. After evaporation, the S1P was re-dissolved by sonication in 20 mM Tris-HCl (pH 8.0) containing equi-molar amounts of r-apoM (SEVVANA et al., *J. Mol. Biol*, 393:920-936 (2009)) or fatty acid free bovine serum albumin (Sigma #A6003), and kept at 4° C. until use. Cell culture. Human umbilical vein endothelial cells (HUVEC, passage 4-10) were cultured as described (HLA et al., *J. Biol Chem.* 265:9308-9313 (1990)). HEK293 cells stably expressing S1P1-GFP (LIU C H et al., *Mol. Biol Cell*, 10:1179-1190 (1990)) were cultured in Dulbecco's modified Eagle's medium with 10% fetal bovine serum. HUVEC cells were serum starved and pretreated with 1 μM VPC4416 for 30 min where indicated (Oo et al., (2007) *J. Biol Chem.*, 282:9082-9089 (2007)). Statistics. Numerical differences were analyzed with two-tailed Student's t test.

Figure 4A:
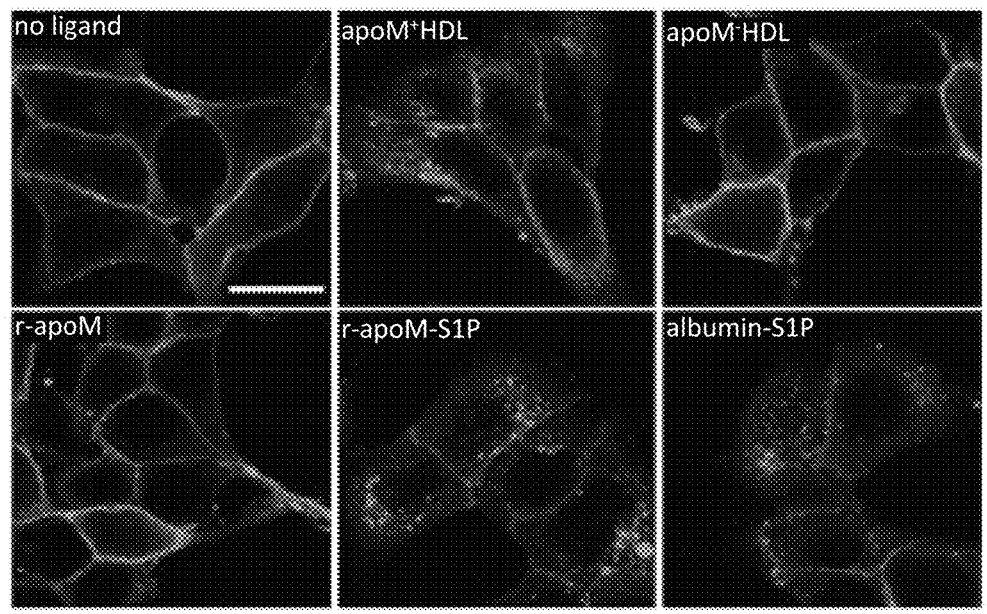
FIG. 4. ApoM-bound S1P activates S1P1-mediated intracellular signaling pathways and affects migration of HUVEC. (A) Confocal microscopy of HEK293 cells stably expressing S1P1-GFP. Cells were serum starved, stimulated for 1 h with indicated ligands, fixed and imaged. $ApoM^+$ HDL (equivalent to ~100 nM S1P as determined by LC/MS/MS) or $ApoM^-HDL$ was used at 100 µg/ml. Fatty acid free BSA and r-apoM were complexed with S1P and used at the final concentration of 100 nM (equimolar for both protein and lipid). Scale bar, 20 µm. (B) HUVEC were serum-starved and pre-treated with 1 µM of the S1P1 antagonist VPC44116 for 30 min before stimulated with $apoM^+HDL$ (20 µg/ml protein, 20 nM S1P), $apoM^-HDL$ (20 µg/ml protein), or albumin-S1P (100 nM S1P and equimolar protein) for 10 min in (B) (Note that, VPC44116 has no inhibitory effects on cells stimulated by FCS, which is because FCS can activate other receptor systems than S1P1). Activation of p44/42, and Akt was examined by western blot analysis using phospho-specific antibodies. (C) HUVEC were serum starved and pre-treated with 1 µM VPC44116 for 30 min where indicated and subjected to migration assay with 10 µg/ml $apoM^+HDL$ (10 nM S1P) or 10 µg/ml $apoM^-HDL$ or 10 nM albumin-S1P. Data are mean±SD, n=3. * p<0.01. (D) Microscopy of HUVEC that were serum starved and stimulated with 100 µg/ml $apoM^+HDL$, $apoM^-HDL$, 100 nM albumin-S1P, r-apoM-S1P or 100 nM S1P-free r-apoM for 1 h. After fixation, VE-cadherin was revealed by immunostaining and confocal immunofluorescence microscopy (green), nuclei (blue), and F-actin (red) was visualized with confocal microscopy. Scale bar, 20 µm. HUVEC were serum starved and stimulated for 5 min with 30 nM albumin-S1P, r-apoM-S1P, 10 µg/mL ApoM+ HDL, or 30 nM S1P-free r-apoM (E) or with increasing concentrations of albumin or r-apoM-S1P (F). Activation of p44/42 and Akt was examined by Western blot analysis using phospho-specific antibodies. (G) HUVEC were serum starved and subjected to migration assay with increasing concentrations of albumin- or r-apoM-S1P. Data are mean±SD (n=3). *P<0.01.
Figure 4D:
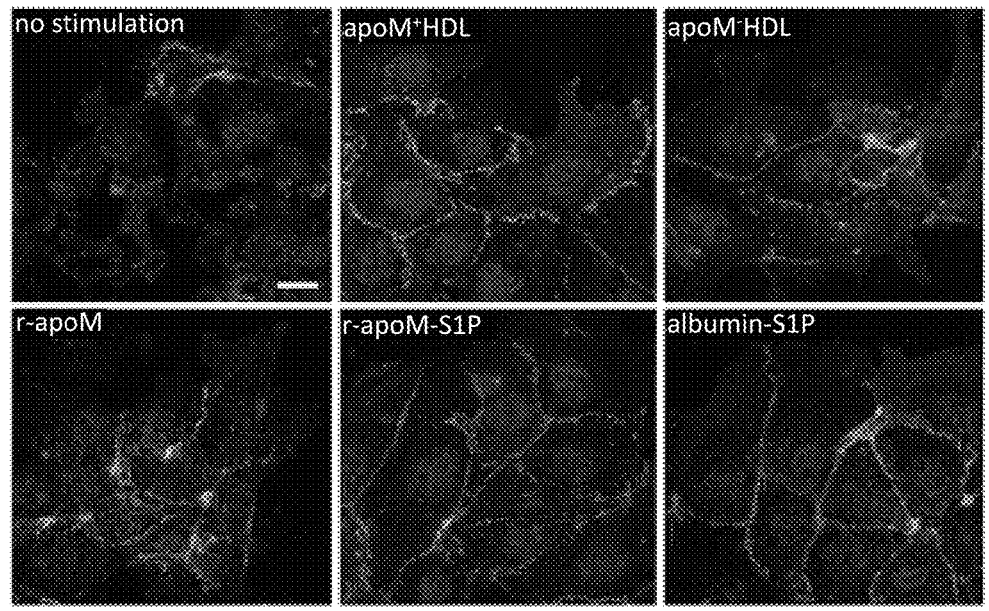
Figures 4E, 4F, 4G:
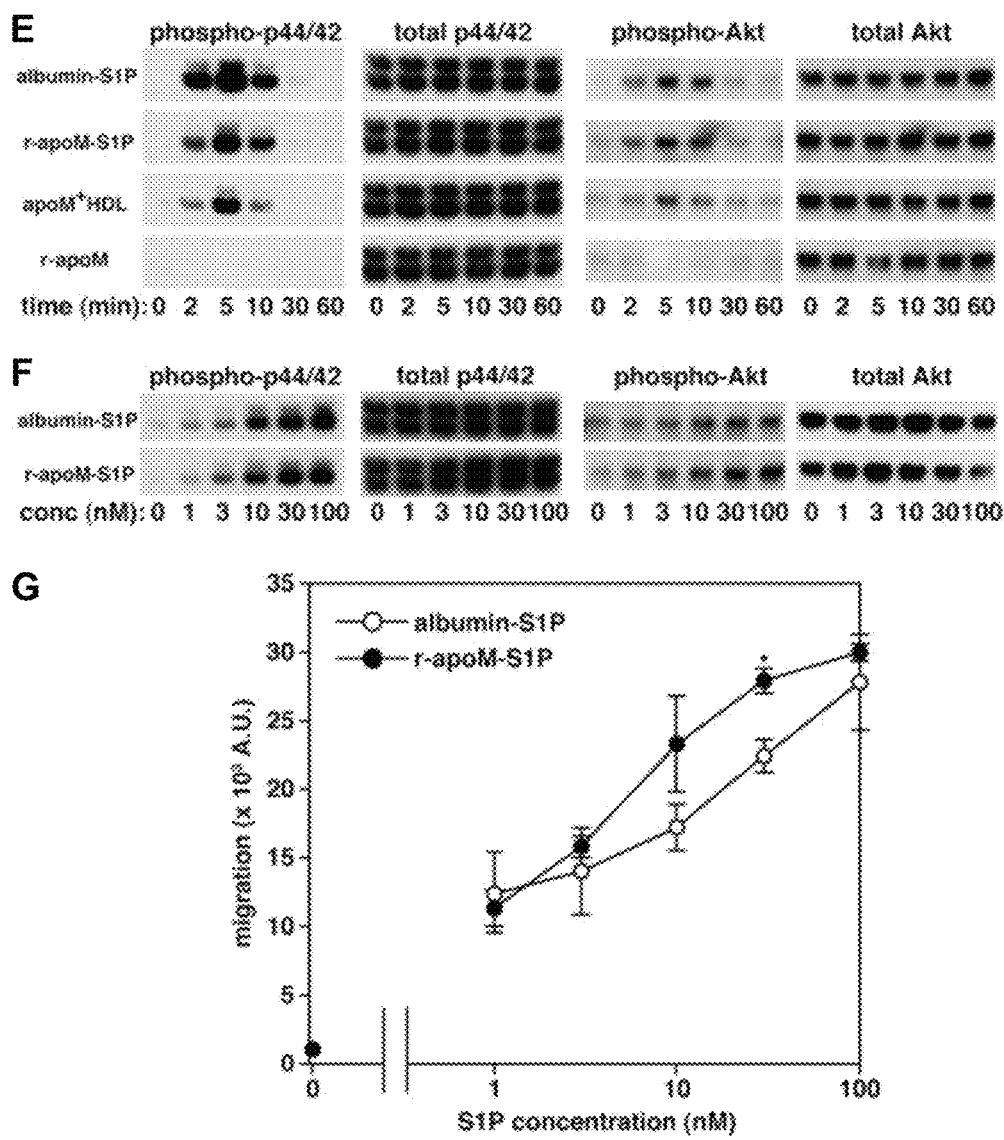

Migration Assays. Migration assays were performed using a 96-well chemotaxis chamber system (Neuroprobe) (MICHAUD et al., *J. Immunol.*, 184:1475-1483 (2010)). After serum starvation for 3 h in M199 medium, HUVEC were placed in the upper well of the chemotaxis chamber at a density of 1×105 cells per well and were allowed to migrate toward chemoattractants in the lower well, which was separated from the upper well by a fibronectin-coated polycarbonate filter with 8-μm pores. After incubation for 4 h at 37° C., the upper surface of the filter was wiped clean of nonmigrating cells, and the cells on the lower surface were stained by 1% crystal violet. The filter was scanned, and the color density of each well was quantified using ImageJ software. ApoM⁺HDL stimulated chemotaxis of HUVEC and this effect was abolished by pre-treatment with the S1P1-antagonist VPC44116 (FIG. 4C). Both albumin- and r-apoM-bound S1P worked as chemoattractants in a concentration-dependent manner, but r-apoM-bound S1P showed a slightly higher activity. (FIG. 4G).

Figure 5:
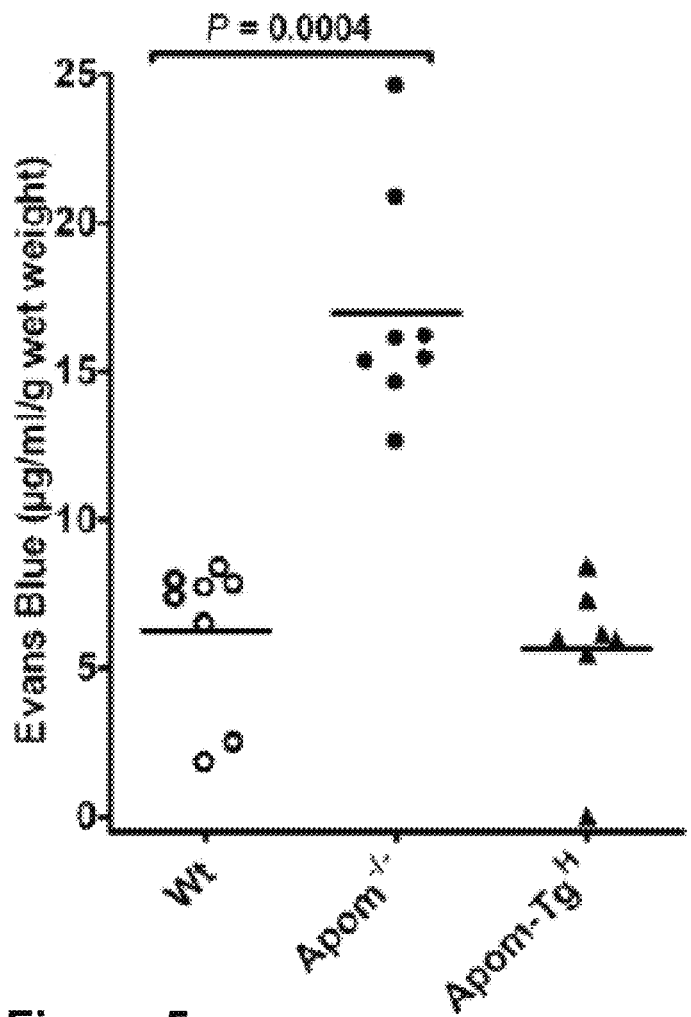
FIG. 5. ApoM-S1P complex maintains lung endothelial barrier function Wt, $Apom^{-/-}$, and $Apom-Tg^H$ mice were injected intravenously with 30 µg Evans Blue per g body weight. After 30 minutes the mice were perfused with saline before the lungs were removed and used for extraction of Evans Blue. Each point represents the content of Evans Blue in the lungs of one individual mouse, and lines represent mean values.
Figure 6:
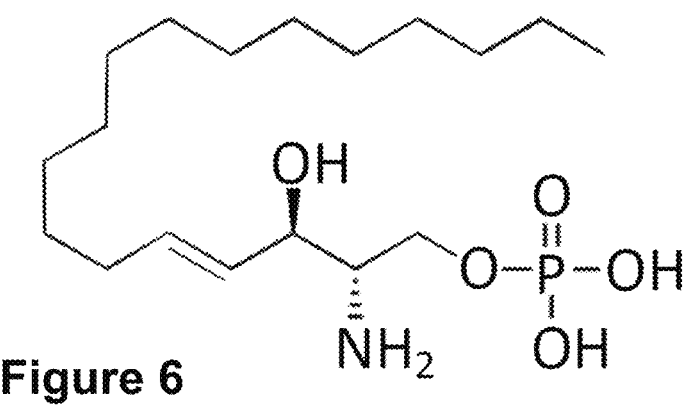
FIG. 6. The molecular structure of S1P.
Figure 7:
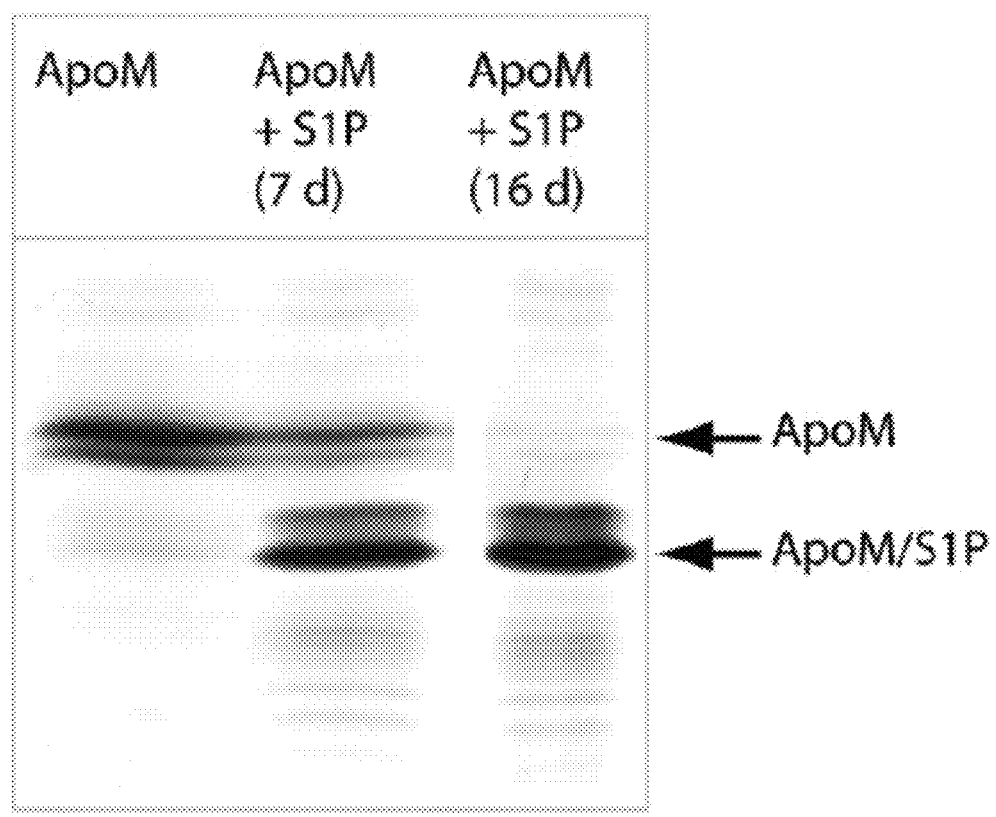
FIG. 7. Isoelectric focusing gel showing the formation of the apoM-S1P complex. Isoelectric focusing gel showing (from left to right) lane 1: apoM in complex with myristic acid (labeled as ApoM); lanes 2 and 3: apoM-S1P complex formation after apoM was incubated with S1P for 7 and 16 d, respectively.

Vascular Permeability. Mice were injected intravenously with 30 μg Evans Blue per gram body weight. After 30 min the mice were anaesthetized and extensively perfused with saline via the right ventricle to remove intravascular Evans Blue. The lungs were weighed (wet weight) and Evans Blue was extracted in 1 ml formamide at 56° C. for 16 hours. Evans Blue concentration was determined from the OD620 minus OD500 in the extract and a serial dilution of a standard. After injection of Evans Blue intravenously in Wt, Apom-Tg$^H$ and Apom$^{-/-}$ mice increased extravasation of Evans Blue in the lung was observed in the Apom$^{-/-}$ mice as compared to Wt and Apom-Tg$^H$ mice (FIG. 5). This suggests that even though Apom$^{-/-}$ mice have albumin-bound S1P in the circulation this cannot fully maintain the endothelial barrier function in the lung.

$S1P_1$ Internalization and Downstream Signalling Assays. HEK293 cells stably expressing S1P1-GFP were plated on 35-mm glass-bottomed dishes and were serum starved for 24 h in DMEM containing 2% charcoal stripped serum followed by starvation for another 2 h in plain DMEM, stimulated as indicated, and fixed with 4% paraformaldehyde. Confocal laser-scanning microscopy analysis was performed using a FluoView FV 10i system (Olympus). Both ApoM⁺HDL and r-apoM-bound S1P induced robust internalization of GFP-S1P1 receptor, similarly to albumin-bound S1P that was used as a positive control (FIG. 4A). Neither apoM⁻HDL nor r-apoM without S1P caused receptor internalization. These data indicate that the apoM/S1P complex can activate the S1P1 receptor whether it is part of an HDL particle or not. To test activation of endogenous S1P1 receptor and the downstream signalling by apoM-bound S1P, human umbilical vein endothelial cells (HUVEC) were stimulated with various carriers complexed or not with S1P. Prominent phosphorylation of p44/42 and Akt was induced by apoM⁺HDL, but not by apoM⁻HDL (FIG. 4B). Moreover, blocking of S1P1-receptors with the S1P1-selective antagonist VPC44116 (Oo et al., (2007) *J. Biol Chem.*, 282:9082-9089 (2007); AWAR et al., *Am J Physiol Renal Physiol.*, 290:F1516-1524 (2006)) essentially abolished the effect of apoM⁺HDL on p44/42 and Akt phosphorylation (FIG. 4B), indicating that the effects of apoM⁺HDL were mediated by the S1P1 receptor. Albumin-bound S1P, apoM⁺HDL and apoM-bound S1P showed a similar time-course and dose-response in the activation of p44/42 and Akt (FIG. 4E-F). Western blotting was done after separation in 10 or 12% SDS-PAGE gels and immunostained with antibodies against human apoM, p44/42, phospho-p44/42 and phospho-Akt (Cell Signalling).

Adherens Junction Assembly Assays. Vascular Endothelial Cadherin Immunostaining was performed on HUVEC that were plated on 35-mm glass-bottomed dishes and serum starved for 24 h in M199 medium containing 1% charcoal-stripped serum. The cells were serum starved for another 2 h in plain M199 medium, stimulated as indicated, and fixed with 4% paraformaldehyde. Immunofluorescence analysis was performed using anti-vascular endothelial cadherin antibody (Santa Cruz) and Alexa Fluor 488-conjugated secondary antibody (Invitrogen). Nuclei were stained with TO-PRO-3 dye (Invitrogen). Confocal laser-scanning microscopy analysis was performed as described above. As shown in FIG. 4D, HUVEC were well-spread, contained F-actin and formed adherens junctions when treated with apoM⁺HDL, as well as with albumin- and r-apoM-bound S1P. In contrast, adherens junctions and F-actin were not efficiently induced by apoM⁻HDL or by r-apoM without S1P.

Example 4

Production of Recombinant ApoM in Membrane Nanolipoparticles

Production of apoM in nanolipoparticles was performed based on the method described by Katzen et al. (*J Proteome*

Res, 7:3535-3542 (2008)). Essentially, recombinant ApoM was expressed in an in vitro translational system supplemented with ApoA1 and phospholipids which spontaneously assembled nascent membrane proteins into nanodiscs, which have similar structure as HDL particles.

Briefly, 1,2-dimyristoyl-sn-glycero-3-phosphocholine, cholate, and His-tagged apoA1 (components of the Membrane Max reagent system obtained Life Technology) and mixed in a molar ratio of 140:280:1 and subjected to 3 temperature shift cycles (RT for 10 min, 30° C. for 10 min, and RT for 90 min). Then, the cholate was removed by incubating with Bio-Beads SM-2 nonpolar polystyrene adsorbents (Bio-Rad). Monodisperse nanolipoparticles were purified by size exclusion chromatography using Superdex 200 10300 GL (GE Healthcare). ApoM was synthesized using a cell-free protein expression system (Expressway Maxi Cell-Free E. coli Expression System, Life Technology), with the addition of the purified nanolipoparticles at a final concentration of 1.35 mg/ml. The soluble fraction was obtained by centrifugation at 14,000×g for 5 min. Since the scaffold protein of the nanolipoparticles, ApoA1, was tagged with the polyhistidine epitope, His-tagged apoA1 containing nanolipoparticles were purified using HisPur Ni-NTA Resin (Thermo Scientific), and the incorporation of apoM was confirmed by Western blot analysis using an anti-apoM antibody (Santa Cruz).

Figure 8A:
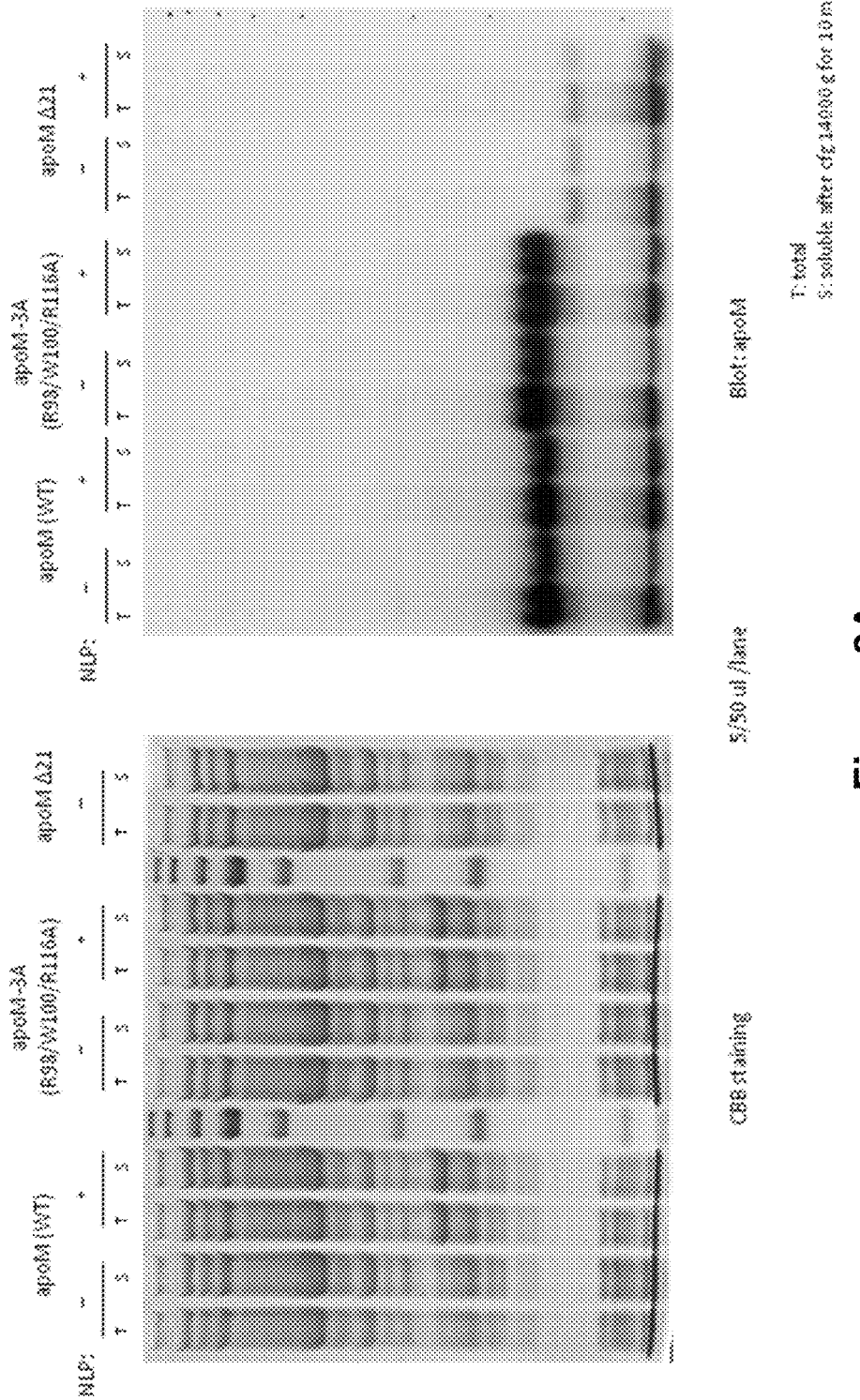
FIG. 8A. Expression of apoM by Membrane Protein Expression System. ApoM (WT, R98A/W100A/R116A, or apoM Δ21) was synthesized using a cell-free protein expression system in the presence or absence of the purified nanolipoparticles (NLP). The soluble fraction was obtained by centrifugation at 14,000 g for 5 min. Left, Coomassie Brilliant Blue staining Right, western blot analysis using anti-apoM antibody.
Figure 8B:
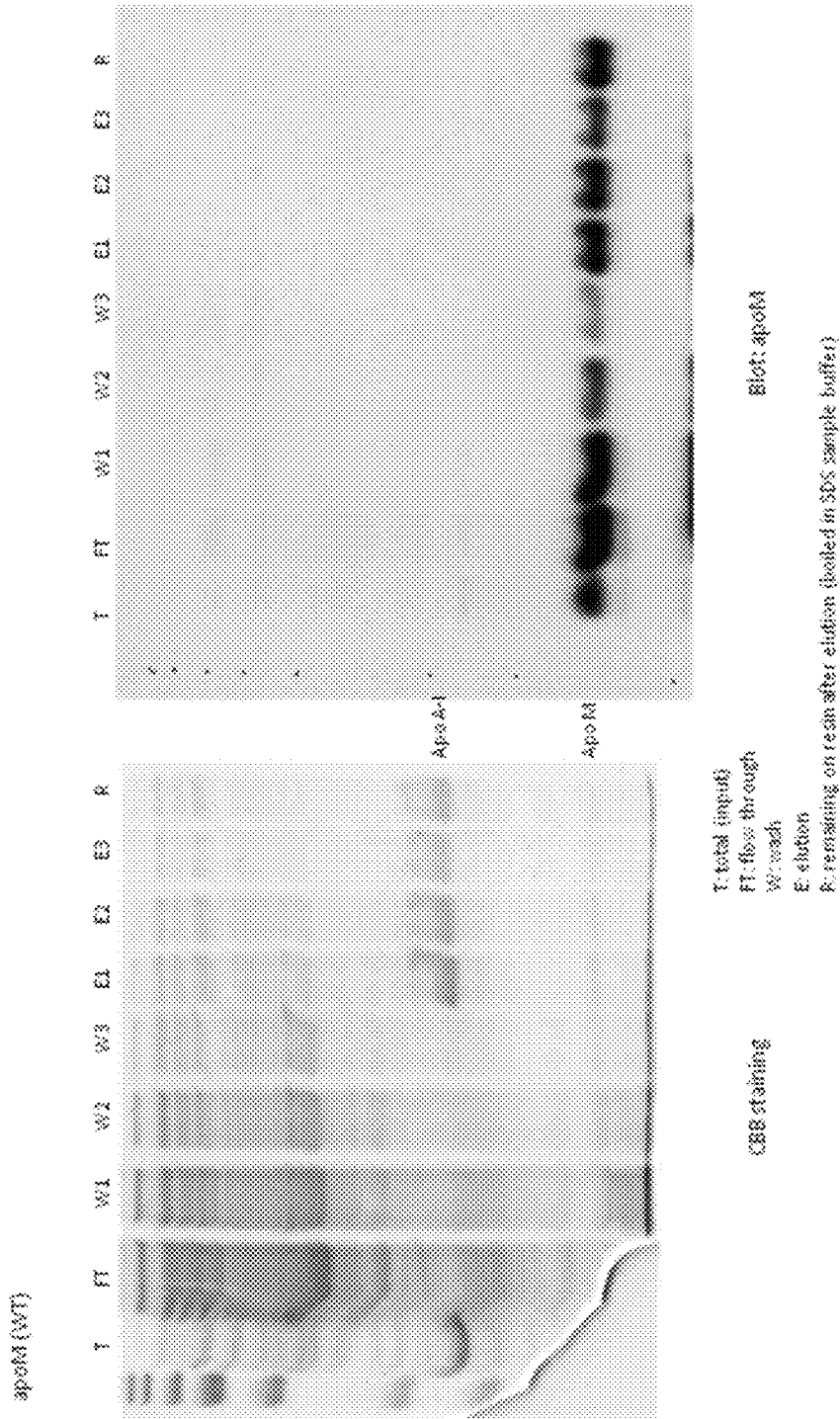
FIG. 8B. Purification of ApoM nanolipoparticles (nanodiscs). His-tagged ApoAI-containing NLP was purified using Ni-NTA resin, and incorporation of apoM was examined. T: total input, FT: flow through, W: wash, E: elution, R: remaining on resin after elution. Left, Coomassie Brilliant Blue staining Right, western blot analysis using anti-apoM antibody.

Three forms of ApoM were expressed: human ApoM, S1P-binding deficient triple mutant ApoM (R98A/W100A/R116A), and N-terminal truncated ApoM in the E. coli-based translational system supplemented with ApoA1 and phospholipids. As shown in FIG. 8A, high level expression of ApoM or the mutant ApoM was observed. In contrast, the N-terminal truncated ApoM did not express significantly. As shown in FIG. 8B, significant amount of ApoM was associated with the nanodiscs suggesting that it was incorporated successfully. This preparation will be useful to conduct therapeutic studies whereby S1P receptors can be targeted by ApoM in the nanodiscs. Similar expression systems can be used to prepare ApoM to target S1P receptors in therapeutic applications.

Example 5

Inhibition of Vascular Inflammation by ApoM

Figure 9:
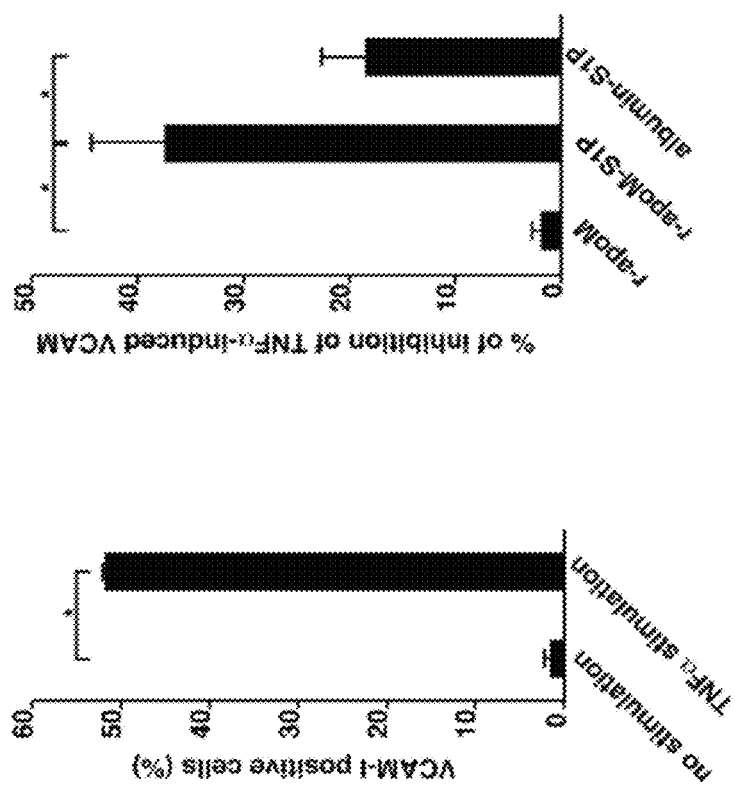
FIG. 9. ApoM/S1P inhibition of endothelial cell VCAM-1 expression. Human umbilical vein endothelial cells (HUVEC) were treated with TNFα for 3 hr. Some cells were co-treated with recombinant (r)ApoM (100 nM) or rApoM/S1P complex (100 nM) or albumin/S1P complex (100 nM) for the same amount of time. The cells were then analyzed for the cell surface expression of Vascular cell adhesion molecule (VCAM)-1 by flow cytometry. Note that ApoM/S1P complex inhibited (~40%) TNFα-induced VCAM-1 expression.

Inflammation of vascular endothelial cells is a critical initiating event in atherosclerosis, which leads to heart attacks and strokes. Endothelial cell inflammation is induced by cytokines such as TNFα and IL-1β. When endothelial cells are exposed to such cytokines, an inflammatory program of gene expression is induced, resulting in the formation of adhesion molecules such as VCAM-1, which in turn is needed for the recruitment of monocytes into the blood vessel wall. The inventors found that treatment of human endothelial cells with ApoM supplemented with S1P resulted in the significant suppression of cytokine-induced VCAM-1 expression. This was not seen if ApoM without S1P was used (FIG. 9) suggesting that ApoM/S1P complex is needed to inhibit cytokine signaling and suppress inflammation. Thus, ApoM/S1P complexes can be used to suppress vascular inflammation as a potential treatment for atherosclerosis.

Example 6

Regulation of Immune Cell Trafficking by ApoM/S1P

S1P receptors, in particular, S1P$_1$ receptor regulates T and B cell trafficking. Specifically, the egress of T and B cells from secondary lymphoid organs require the presence of S1P$_1$ in the immune cells which sense the S1P gradient to leave tissues into the circulatory system. This process is key in many diseases such as multiple sclerosis, where autoreactive immune cells attack the neuronal tissues, leading to significant disability. The S1P$_1$ inhibitor FTY720/Fingolimod/Gilenya™ is now approved as a therapeutic in multiple sclerosis. In addition, this class of drugs may be useful in other autoimmune indications such as psoriasis, rheumatoid arthritis, uveitis and type I diabetes.

Figure 10:
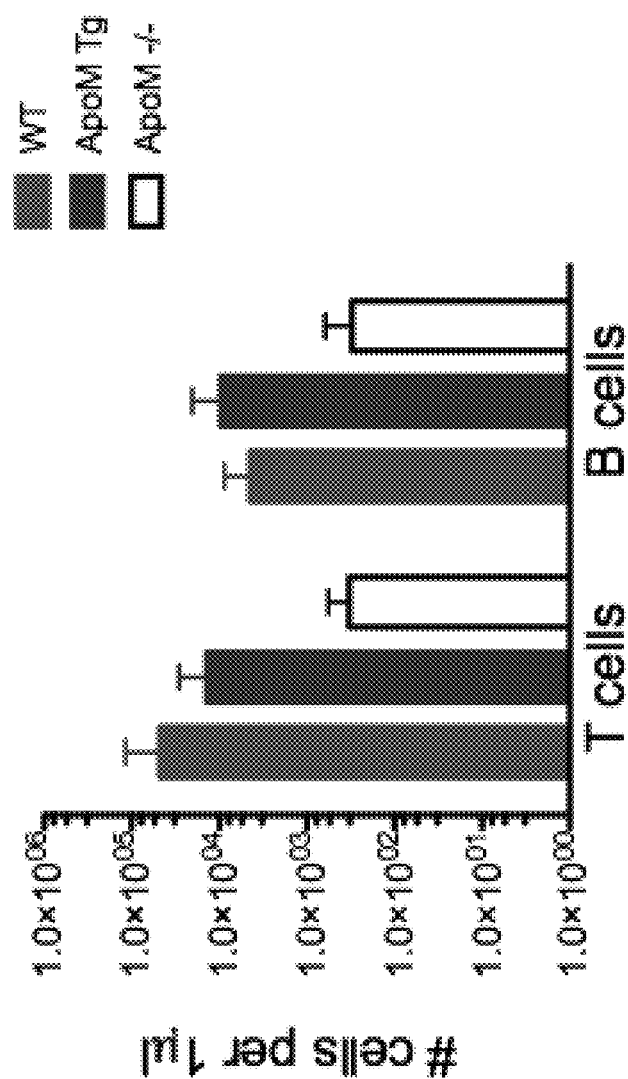
FIG. 10. Numbers of T and B cells from wild-type, ApoM knock out and ApoM transgenic mice.

To test if ApoM/S1P complex has a role in immune cell trafficking, Lymph was collected as described (PHAM et al., J Exp. Med., 207:17-27 (2010)) from wild-type, ApoM knock out and ApoM transgenic mice. One microliter of lymph was used to isolate cells, and T and B cell numbers in lymph were quantified by FACS. As shown in FIG. 10, both T cells and B cells were greatly depressed in ApoM KO mice, suggesting that ApoM/S1P signaling is needed for optimal egress of immune cells from secondary lymphoid organs into lymph. Since S1P$_1$ receptor is required for this process and since ApoM is a physiological carrier for S1P, these data strongly suggest that the S1P/ApoM complex plays a critical role in lymphocyte egress, and therefore therapeutic inhibition of the ApoM/S1P system can result in inhibition of immune reactions which is useful in the treatment of autoimmune diseases such as multiple sclerosis, psoriasis, rheumatoid arthritis, uveitis and type I diabetes.

```
Protein sequence for apolipoprotein
M >gi|22091452|ref|NP_061974.2| [Homo sapiens]
                                       SEQ ID NO: 1
MFHQIWAALLYFYGIILNSIYQCPEHSQLTTLGVDGKEFPEVHLGQWYF

IAGAAPTKEELATFDPVDNIVFNMAAGSAPMQLHLRATIRMKDGLCVPR

KWIYHLTEGSTDLRTEGRPDMKTELFSSSCPGGIMLNETGQGYQRFLLY

NRSPHPPEKCVEEFKSLTSCLDSKAFLLTPRNQEACELSNN

Protein sequence for apolipoprotein
M >gi|9055162|ref|NP_061286.1| [Mus musculus]
                                       SEQ ID NO: 2
MFHQVWAALLSLYGLLFNSMNQCPEHSQLTALGMDDTETPEPHLGLWYF

IAGAASTTEELATFDPVDNIVFNMAAGSAPRQLQLRATIRTKSGVCVPR

KWTYRLTEGKGNMELRTEGRPDMKTDLFSSSCPGGIMLKETGQGYQRFL

LYNRSPHPPEKCVEEFQSLTSCLDFKAFLVTPRNQEACPLSSK
*The underlined portion represent the signal peptide in the
respective protein.
```

What is claimed is:

1. A method of treating or reducing the risk of developing a disease associated with endothelial injury in a subject, comprising administering a therapeutically effective amount of a composition comprising full-length ApoM, wherein said full-length ApoM is recombinantly produced.

2. The method of claim 1, wherein said ApoM is incorporated in a HDL-like nanostructure.

3. The method of claim 2, wherein said HDL-like nanostructure comprises ApoA1 and phospholipids.

4. The method of claim 3, wherein said phospholipids comprise phosphocholine.

5. The method of claim 1, wherein said composition further comprises S1P which forms a complex with said ApoM.

6. The method of claim 1, wherein said composition comprises ApoM-containing HDLs isolated from human plasma, and S1P which forms a complex with the ApoM in HDLs.

7. The method of claim 1, wherein said disease associated with endothelial injury is selected from the group consisting of atherosclerosis, ischemic cardiovascular disease, stroke, vital organ failure after ischemic stress, ischemic peripheral vascular disease, peripheral vascular disorders associated with diabetes, vascular leak syndrome, autoimmune vasculitis, adult (acute) respiratory distress syndrome, acute lung injury, ventilator-induced pneumonia, Dengue hemorrhagic fever, SARs, influenza, swine flu, thrombocytopenia, hemangioma, inflammatory diseases, malaria, sickle cell anemia, dialysis-induced vascular injury, diabetic retinopathy, wet age-related macular degeneration, and sepsis.

8. A method of reducing a side effect of Fingolimod in a patient being treated with Fingolimod for an autoimmune disorder, comprising administering ApoM to the patient.

9. The method of claim 8, wherein said ApoM is provided in resconstituted HDL-like nanostructures.

10. A composition comprising reconstituted HDL-like nanostructures integrated with an isolated ApoM/S1P complex, wherein said ApoM is full-length ApoM.

11. The composition of claim 10, wherein said composition comprises ApoM-containing HDLs isolated from human plasma, and S1P which forms said complex with the ApoM in HDLs.

12. A composition comprising reconstituted HDL-like nanostructures integrated with recombinantly produced full-length ApoM.

13. The composition of claim 12, wherein said reconstituted HDL-like nanostructures comprise ApoA1 and phospholipids.

14. The composition of claim 12, further comprising S1P which forms a complex with ApoM in the nanostructures.

\* \* \* \* \*

SEQUENCE LISTING

<160> NUMBER OF SEQ ID NOS: 2

<210> SEQ ID NO 1
<211> LENGTH: 188
<212> TYPE: PRT

<213> ORGANISM: Homo sapiens

<400> SEQUENCE: 1

```
Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
            20                  25                  30

Gly Val Asp Gly Lys Glu Phe Pro Glu Val His Leu Gly Gln Trp Tyr
        35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185
```

<210> SEQ ID NO 2
<211> LENGTH: 190
<212> TYPE: PRT
<213> ORGANISM: Mus musculus

<400> SEQUENCE: 2

```
Met Phe His Gln Val Trp Ala Ala Leu Leu Ser Leu Tyr Gly Leu Leu
1               5                   10                  15

Phe Asn Ser Met Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Ser Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Gln Ser Leu Thr Ser Cys Leu Asp Phe Lys Ala Phe Leu
```

```
                165                 170                 175
Val Thr Pro Arg Asn Gln Glu Ala Cys Pro Leu Ser Ser Lys
            180                 185                 190
```